United States Patent [19]
Eran et al.

[11] Patent Number: 5,739,293
[45] Date of Patent: Apr. 14, 1998

[54] $A_1$-ACID GLYCOPROTEIN PURIFICATION PROCESS AND PRODUCT

[75] Inventors: Harutyun Eran, Northridge; Qiang Xu, Alhambra, both of Calif.

[73] Assignee: Alpha Therapeutic Corporation, Los Angeles, Calif.

[21] Appl. No.: 626,598

[22] Filed: Apr. 2, 1996

Related U.S. Application Data

[63] Continuation of Ser. No. 422,631, Apr. 14, 1995, abandoned, which is a continuation of Ser. No. 121,781, Sep. 15, 1993, abandoned.

[51] Int. Cl.$^6$ .......................... C07K 1/18; C07K 14/47; C07K 14/745
[52] U.S. Cl. .......................... 530/416; 530/380; 530/386; 530/412
[58] Field of Search ..................... 530/380, 386, 530/395, 397, 412, 415, 416, 831

[56] References Cited

PUBLICATIONS

Succari, et al., "Chrombio 2573", Journal of Chromatography, 341 (1985) 457–461.
Cohn et al. Am J. Chem. Soc. 68 459–475 1946.
Hao et al. Biochem Biophysics Acta 322 99–108 1973.
Cohn et al. Am J. Chem. Soc. 72 465–474 1950.
Schmid Am J Chem Soc. 75 60–68 1953.
Taira et al. Am J Vet Res. 53(6) 961–956 1992.
Harris et al. Protein Purification Methods 57–64 1991.

Cohn, EJ et al. "Preparation & Properties of Serum & Plasma Proteins IV. A System for the Separation into Fractions of the Protein & Lipoprotein Components of Biological Tissues & Fluids" Am. J. Chem. Soc. 68:459–475 1946.
Hao, Yu–Lee et al. "Development of Large Scale Fractionation Methods IV. A Simple Method for the Large Scale Preparation of $\alpha_1$,–Acid Glycoprotein " Biochim Biophys Acta 322:99–108 1973.
Cohn EJ et al. "A System for the Separation of the Components of Human Blood: Quantitative Procedures for the Separation of The Protein Components of Human Plasma" Am J. Chem Soc. 72:465–474 1950.
Schmid, K. "Preparation & Properties of Serum & Plasma Proteins. XXIX. Separation From Human Plasma of Polysaccherides, Peptides & Proteins of Low Molecular Weight Crystallization of An Acid Glycoprotein" Am. J. Chem. Soc. 75:60–68 1953.
Taira, et al."Isolation and Charactrerization of $\alpha_1$–Acid Glycoprotein from Horses, & its Evaluation as an Acute–Phase Reactive Protein in Horses" Am J. Vet Res 53(6)961–965 1992.
Harris et al. "Protein Purification Methods" pp. 57–64 1991.

*Primary Examiner*—Nancy Degen
*Attorney, Agent, or Firm*—Christie, Parker & Hale, LLP

[57] ABSTRACT

Purified $\alpha_1$-acid glycoprotein and a process for preparing purified $\alpha_1$-acid glycoprotein. The process comprises providing an impure protein fraction, binding contaminants, but not $\alpha_1$-acid glycoprotein, to a cation-exchange medium, and binding $\alpha_1$-acid glycoprotein to an anion-exchange medium, and eluting the $\alpha_1$-acid glycoprotein from the anion-exchange medium.

36 Claims, No Drawings

$A_1$-ACID GLYCOPROTEIN PURIFICATION PROCESS AND PRODUCT

CROSS-REFERENCE TO RELATED APPLICATION

This is a continuation of application Ser. No. 08/422,631, filed Apr. 14, 1995, now abandoned, which is a continuation of application Ser. No. 08/121,781, filed Sep. 15, 1993, now abandoned.

FIELD OF THE INVENTION

This invention relates to methods useful for the separation of $\alpha_1$-acid glycoprotein from other proteins found in plasma.

BACKGROUND OF THE INVENTION

Alpha$_1$-acid glycoprotein, also known as orosomucoid, is present in normal plasma at a concentration of about 55–140 mg/dl. The protein has a molecular weight of about 40,000, a pI of about 2.7 and has a high carbohydrate content, of about 42%. The function of $\alpha_1$-acid glycoprotein remains unknown although it is known to bind hormones such as progesterone.

Alpha$_1$-acid glycoprotein has been found to be useful as a carrier for pharmacologically active substances, for delivery to a target tissue. In particular, purified $\alpha_1$-acid glycoprotein may be chemically modified with sulfuric acid to remove part of the carbohydrate from the protein portion of the $\alpha_1$-acid glycoprotein molecule. Lysine is then bound to the remaining carbohydrate groups and DNA, encoding a desired gene, is bound to the lysine residues for delivery of a specific gene to a target tissue.

It has been found that $\alpha_1$-acid glycoprotein, treated in this manner is specific for receptors on the liver and, therefore, acts as a means for targeting and delivering genes to the liver.

The gene therapy method described above requires the use of purified $\alpha_1$-acid glycoprotein. Methods previously used for purifying $\alpha_1$-acid glycoprotein, which have used dialyzed plasma as a starting material and DEAE- and CM-Trisacryl purification, have produced $\alpha_1$-acid glycoprotein preparations of only low purity. In one case the highest purity reported was only 50%. For use as a gene therapy delivery molecule it is desirable that the $\alpha_1$-acid glycoprotein is of a very high purity. Contaminating proteins in the $\alpha_1$-acid glycoprotein preparation may interact with the reactants of the chemical modification used for binding the desired gene to the $\alpha_1$-acid glycoprotein and may result in undesirably low binding efficiencies of the DNA to the $\alpha_1$-acid glycoprotein. Also, since only a limited amount of material can be injected into a patient, and since only DNA bound to $\alpha_1$-acid glycoprotein is effective in delivering the desired gene to the target tissue, contaminating proteins reduce the amount of DNA which can be delivered per treatment. Therefore, there is a need for a purification procedure for the preparation of high purity $\alpha_1$-acid glycoprotein.

The present invention describes a process for the preparation of high purity $\alpha_1$-acid glycoprotein.

SUMMARY OF THE INVENTION

The present invention describes a purified $\alpha_1$-acid glycoprotein and a process for preparing the purified $\alpha_1$-acid glycoprotein.

The process comprises providing an impure protein fraction, binding $\alpha_1$-acid glycoprotein to an anion-exchange medium, and eluting the $\alpha_1$-acid glycoprotein from the anion-exchange medium.

In one embodiment of the invention the process further comprises contacting the impure protein fraction with a cation-exchange medium and binding contaminants, but not $\alpha_1$-acid glycoprotein, to the cation-exchange medium.

$\alpha_1$-acid glycoprotein prepared by the process of the present invention is about 99% pure.

DETAILED DESCRIPTION

The present invention provides processes for the separation of $\alpha_1$-acid glycoprotein from an impure protein fraction which contains $\alpha_1$-acid glycoprotein and undesirable contaminants. The impure protein fraction used as the starting material for the $\alpha_1$-acid glycoprotein purification process may be the Fraction V precipitate or the Fraction V supernatant from the Cohn fractionation method (Cohn et al., *J. Amer. Chem. Soc.*, 68 459–475, 1946; also U.S. Pat. No. 2,710,294, both incorporated herein by reference) other blood-plasma-derived fractions, a composition derived from recombinant-DNA techniques or other suitable fractions containing $\alpha_1$-acid glycoprotein.

In accordance with the practice of this invention, high-purity $\alpha_1$-acid glycoprotein solutions are provided by removing contaminants from the impure protein fraction. The contaminants are removed by anion or anion- and cation-exchange chromatography.

If necessary, the impure protein fraction is adjusted to a pH value above about 3. At this pH the $\alpha_1$-acid glycoprotein, which has a pI of 2.7, is negatively charged. In an exemplary embodiment of the practice of this invention either Fraction V precipitate or supernatant, prepared by the Cohn cold ethanol process, is used as the impure protein fraction for the purification of $\alpha_1$-acid glycoprotein. When the Fraction V precipitate or supernatant are used the pH of the supernatant or the precipitate, when resuspended in distilled water, is about 4.1 to 4.5 and can be used without adjustment of the pH. In one embodiment of the present invention the pH of the impure protein fraction is adjusted to a pH of about 4.5 to about 4.7.

In one embodiment of the present invention, the impure protein fraction is applied to an anion-exchange medium. The $\alpha_1$-acid glycoprotein present in the impure protein fraction binds to the anion-exchange medium. The anion-exchange medium is then washed to remove any unbound material from the anion-exchange medium. After the unbound material is removed, $\alpha_1$-acid glycoprotein is eluted and the eluate is collected.

In another embodiment of the present invention the eluate from the anion-exchange medium is collected and then contacted with a cation-exchange medium and then bound to an anion-exchange medium, as described below.

In another embodiment of the present invention, the impure protein fraction is contacted with a cation-exchange medium, prior to binding the $\alpha_1$-acid glycoprotein to the anion-exchange medium. Since $\alpha_1$-acid glycoprotein is negatively charged, it will not bind to a cation-exchange medium, instead it remains in solution. Contaminants contained in the impure protein fraction which are positively charged bind to the cation-exchange medium and are removed. The unbound fraction is collected by filtration.

The unbound fraction is then applied to an anion-exchange medium. The $\alpha_1$-acid glycoprotein binds to the anion-exchange medium and the medium is washed to remove unbound proteins. After the unbound proteins are removed, $\alpha_1$-acid glycoprotein is eluted from the anion-exchange medium. The eluate is collected.

In a preferred embodiment of the present invention $\alpha_1$-acid glycoprotein is eluted from the anion-exchange medium using a high salt solution, such a 1M NaCl in a suitable aqueous solution. Alpha$_1$-acid glycoprotein eluted from the anion-exchange medium is recovered, concentrated and washed, by diafiltration/ultrafiltration or other suitable method, to provide a final purified $\alpha_1$-acid glycoprotein solution.

The $\alpha_1$-acid glycoprotein solution prepared in accordance with the process of the present invention is of very high purity, i.e., greater than 99% of the protein present in the solution is $\alpha_1$-acid glycoprotein.

Any of a variety of anion-exchange mediums can be used in accordance with this invention to purify $\alpha_1$-acid glycoprotein. Such mediums include those sold under the trade names "DEAE-SEPHADEX," "DEAE-SEPHAROSE FF," and "Q-SEPHAROSE FF," by Pharmacia Company of Uppsala, Sweden, and "DE52 CELLULOSE," sold by Whatman International Ltd. of Maidstone, England. In one exemplary embodiment of practice of this invention, a diethylamino ethyl (DEAE) ligand bound to high-porosity, cross-linked dextran, DEAE-SEPHADEX A-50 medium, is used.

Any of a variety of cation-exchange mediums can be used in accordance with this invention to purify $\alpha_1$-acid glycoprotein. Such mediums include those sold under the trade names "SP-SEPHADEX," "CM-SEPHAROSE," and "S-SEPHAROSE," by Pharmacia Company of Uppsala, Sweden, and "CM CELLULOSE," sold by Whatman International Ltd. of Maidstone, England. In one exemplary embodiment of practice of this invention, a carboxymethyl (CM) ligand, bound to fibrous cellulose, is used.

Either column chromatography or batch chromatography may be used for the purification of $\alpha_1$-acid glycoprotein. In a preferred embodiment of the present invention batch chromatography is used with the cation- and anion-exchange media.

EXAMPLE 1

Preparation of Fraction V Precipitate and Supernatant

The pH of 3438 kg of human plasma was adjusted to about pH 7 using a 0.8M sodium acetate solution adjusted to a pH of 4.0 with acetic acid, and then mixed for 15 min. The pH 7 plasma was then brought to an ethanol concentration of 8% (vol/vol) by the addition of cold, about −15° C., 95% (vol/vol) ethanol. The temperature of the 8% ethanol solution was gradually reduced to from about −1° C. to about −3° C. as the cold ethanol solution was added. The 8% ethanol solution was mixed for about 15 min., during which time the Fraction I precipitated. The pH of the 8% ethanol solution was adjusted to 6.8 by the addition of a 0.8M sodium acetate solution adjusted to a pH of 4.0 with acetic acid. The resulting solution was mixed for about 15 min. and then brought to about 20% (vol/vol) ethanol by the addition of cold, about −15° C., 95% (vol/vol) ethanol. The temperature of the 20% ethanol solution was gradually reduced to from about −4° C. to about −6° C. as the cold ethanol solution was added. The 20% ethanol solution was mixed for about 60 min., during which time Fraction II+III precipitated. The Fractions I and II+III precipitates were removed by centrifugation and the supernatant retained. The pH of the 20% ethanol supernatant, which contained $\alpha_1$-acid glycoprotein, was then adjusted to 5.2 by the addition of a 0.8M sodium acetate solution adjusted to a pH of 4.0 with acetic acid, containing about 20% (vol/vol) ethanol. The resulting solution was mixed for about 2 hours at from about −4° C. to about −6° C., during which time the Fraction IV$_1$ precipitated. The pH was then adjusted to 5.8 with 1M sodium bicarbonate buffer, and mixing was continued for an additional 15 min. The 20% ethanol solution was then brought to about 40% ethanol (vol/vol) by the addition of cold, about −15° C., 95% ethanol (vol/vol). The addition of ethanol raised the pH to from about 5.9 to about 5.95. The 40% ethanol solution was mixed for 2 hours at from about −4° C. to about −6° C., during which time Fraction IV$_4$ precipitated. The Fractions IV$_1$ and IV$_4$ precipitates were removed by centrifugation, and the supernatant retained.

The 40% ethanol supernatant, which contained $\alpha_1$-acid glycoprotein, was processed further for the collection of the Fraction V precipitate. To precipitate Fraction V, the pH of the 40% ethanol supernatant was adjusted to 4.8 with a 0.8M sodium acetate solution adjusted to a pH of 4.0 with acetic acid, the temperature of the solution was reduced to from about −6° C. to about −12° C., and the solution was mixed for about 2 hours. The Fraction V precipitate was removed by centrifugation, and the resultant Fraction V precipitate and Fraction V supernatant were stored at −15° C. until required.

EXAMPLE 2

Separation of $\alpha_1$-Acid Glycoprotein from Fraction V Precipitate

Fraction V precipitate, prepared in accordance with a process such as that described in Example 1, is mixed with 2 kg of distilled water, for every kg of Fraction V precipitate, at a temperature of 7° C. When the precipitate is completely reconstituted, the protein concentration is adjusted to 9% by adding cold, distilled water. The protein concentration of the resuspended Fraction V precipitate is determined by its refractive index.

One and a half grams of DEAE-SEPHADEX A-50 (the anion-exchange medium, hydrated and equilibrated in accordance with the manufacturers instructions with distilled water and as described in U.S. Pat. No. 5,250,662, which is incorporated herein by reference in its entirety) for each kg of Fraction V precipitate is added to the resuspended Fraction V precipitate and the mixture is gently agitated for 4 hours at 5° C. A quantity of 2.5 g of CELITE 512 powder per kg of Fraction V precipitate is added, and the solution is mixed for an additional 15 minutes. The suspension, which contains DEAE-SEPHADEX A-50 medium-bound $\alpha_1$-acid glycoprotein, is collected by filtering through ZETA PLUS 10C and 90SP, 0.4 and 0.2 micron membranes, sold by Cuno, Inc. of Meriden, Conn. Alpha$_1$-acid glycoprotein is eluted from the DEAE-SEPHADEX A-50 medium by washing the medium with 1M NaCl. The eluate is collected.

The eluate is diafiltered/ultrafiltered in a MILLIPORE PELLICON cassette 10K NMWL, supplied by the Millipore Products Division of Millipore Corp., Bedford, Mass.

EXAMPLE 3

Separation of $\alpha_1$1-Acid Glycoprotein from Fraction V Supernatant

Twenty liters of Fraction V supernatant, prepared in accordance with a process such as that described in Example 1, was mixed with 300 ml of CM-cellulose (the cation-exchange medium hydrated and equilibrated in accordance with the manufacturers instructions with distilled water) for 90 minutes at 5° C. A quantity of 2.5 g of CELITE 512 powder per kg of Fraction V precipitate was added, and the solution was mixed for an additional 15 minutes. The CM-cellulose, and the contaminants bound to the CM-cellulose, was removed by filtration through ZETA PLUS 10C and 90SP, 0.4 and 0.2 micron membranes. A sample of the filtrate was analyzed by SDS gel electrophoresis. The results indicated that the $\alpha_1$-acid glycoprotein was at least at this stage greater than 90% pure.

The filtrate was collected and mixed with 300 ml of hydrated DEAE-SEPHADEX for 90 minutes to bind $\alpha_1$-acid glycoprotein to the DEAE-SEPHADEX. A quantity of 2.5 g of CELITE 512 powder per kg of Fraction V precipitate was added, and the solution was mixed for an additional 15 minutes. The suspension, which contains DEAE-SEPHADEX A-50 medium-bound $\alpha_1$-acid glycoprotein, was collected by filtering through ZETA PLUS 10C and 90SP, 0.4 and 0.2 micron membranes. Alpha$_1$-acid glycoprotein was eluted from the DEAE-SEPHADEX A-50 medium with 5 l of 1M NaCl in distilled water. The eluate was collected.

The eluate was diafiltered/ultrafiltered in a MILLIPORE PELLICON cassette 10K NMWL against distilled water.

EXAMPLE 4

Separation of $\alpha_1$-Acid Glycoprotein from Fraction V Precipitate

Fraction V precipitate, prepared in accordance with a process such as that described in Example 1, is mixed into 2 kg of distilled water, for every kg of Fraction V precipitate, at a temperature of 7° C. When the precipitate is completely reconstituted, the protein concentration is adjusted to 9% by adding cold, distilled water. The amount of protein comprising the Fraction V precipitate is determined by refractive index.

One and a half grams of DEAE-SEPHADEX A-50 (hydrated and equilibrated with distilled water) is added to the first aqueous solution and gently agitated for 4 hours at 5° C. A quantity of 2.5 g of CELITE 512 powder per kg of Fraction V precipitate is added, and the solution is mixed for an additional 15 minutes. The suspension, which contains DEAE-SEPHADEX A-50 medium-bound $\alpha_1$-acid glycoprotein, is collected by filtering through ZETA PLUS 10C and 90SP, 0.4 and 0.2 micron membranes. Alpha$_1$-acid glycoprotein is eluted from the DEAE-SEPHADEX A-50 medium with 1M NaCl and the eluate is collected.

The eluate is diafiltered/ultrafiltered against distilled water in a MILLIPORE PELLICON cassette 10K NMWL.

One volume of the diafiltered eluate is mixed with 0.1 volume of CM-cellulose (hydrated and equilibrated with distilled water) for 90 minutes at 5° C. A quantity of 2.5 g of CELITE 512 powder per kg of Fraction V precipitate is added, and the solution is mixed for an additional 15 minutes. The CM-cellulose, with bound contaminants, is removed by filtration through ZETA PLUS 10C and 90SP, 0.4 and 0.2 micron membranes.

The filtrate is collected and mixed with 0.1 volume of hydrated DEAE-SEPHADEX for 90 minutes to bind $\alpha_1$-acid glycoprotein to the DEAE-SEPHADEX. Alpha$_1$-acid glycoprotein is eluted from the DEAE-SEPHADEX A-50 medium with 1M NaCl in distilled water. The eluate is collected.

The eluate is diafiltered/ultrafiltration in a MILLIPORE PELLICON cassette 10K NMWL against distilled water.

EXAMPLE 5

Analysis of Purified $\alpha_1$-Acid Glycoprotein

The purified $\alpha_1$-acid glycoprotein fraction, prepared in Example 3, was subjected to SDS polyacrylamide gel electrophoresis to determine the purity of the $\alpha_1$-acid glycoprotein. From SDS gels, stained with Coomassie blue, it was estimated that the $\alpha_1$-acid glycoprotein was at least 99% pure, i.e. at least 99% of the protein in the purified $\alpha_1$-acid glycoprotein fraction was $\alpha_1$-acid glycoprotein.

The $\alpha_1$-acid glycoprotein fraction was also analyzed by a 4-rate nephelometry and by radial immunodiffusion. These methods also indicated that $\alpha_1$-acid glycoprotein was at least 99% pure.

The above descriptions of exemplary embodiments of processes for producing $\alpha_1$-acid glycoprotein are for illustrative purposes. Because of variations which will be apparent to those skilled in the art, the present invention is not intended to be limited to the particular embodiments described above. The scope of the invention is defined by the following claims.

What is claimed is:

1. A process for purifying $\alpha_1$-acid glycoprotein comprising:

providing an impure protein fraction comprising $\alpha_1$-acid glycoprotein;

contacting the impure protein fraction with a cation-exchange medium to thereby bind contaminants but not $\alpha_1$-acid glycoprotein to the said cation-exchange medium;

collecting proteins contained in the impure protein fraction which do not bind to the cation-exchange medium;

binding $\alpha_1$-acid glycoprotein present in the unbound protein fraction to an anion-exchange medium; and eluting the $\alpha_1$-acid glycoprotein from the anion-exchange medium.

2. A process as recited in claim 1 wherein the $\alpha_1$-acid glycoprotein is eluted from the anion-exchange medium with a solution comprising sodium chloride.

3. A process as recited in claim 2 wherein the concentration of sodium chloride in the sodium chloride solution is 1M.

4. A process as recited in claim 1 wherein the impure protein fraction comprises Fraction V supernatant.

5. A process as recited in claim 1 wherein the impure protein fraction comprises Fraction V precipitate.

6. A process as recited in claim 1 wherein the anion-exchange medium used to bind $\alpha_1$-acid glycoprotein is a diethylamino ethyl ligand bound to a cross-linked dextran matrix.

7. A process as recited in claim 1 wherein the cation-exchange medium used to bind contaminants is a carboxymethyl ligand bound to a fibrous cellulose matrix.

8. A process for purifying $\alpha_1$-acid glycoprotein comprising:

providing an impure protein fraction comprising $\alpha_1$-acid glycoprotein and protein contaminants;

contacting the impure protein fraction with a first anion-exchange medium to thereby bind $\alpha_1$-acid glycoprotein present in the impure protein fraction to the anion-exchange medium;

eluting $\alpha_1$-acid glycoprotein from the anion-exchange medium to provide an $\alpha_1$-acid glycoprotein eluate;

contacting the $\alpha_1$-acid glycoprotein eluate with a cation-exchange medium to thereby bind contaminants but not $\alpha_1$-acid glycoprotein to said cation exchange medium;

recovering the unbound $\alpha_1$-acid glycoprotein from the cation-exchange medium;

binding $\alpha_1$-acid glycoprotein recovered from the cation exchange medium to a second anion-exchange medium; and eluting the $\alpha_1$-acid glycoprotein from the second anion-exchange medium and recovering the $\alpha_1$-acid glycoprotein.

9. A process as recited in claim 8 wherein the $\alpha_1$-acid glycoprotein is eluted from both the first and second anion-exchange media with a solution comprising sodium chloride.

10. A process as recited in claim 9 wherein the concentration of sodium chloride in the sodium chloride solution is 1M.

11. A process as recited in claim 8 wherein the impure protein fraction comprises Fraction V supernatant.

12. A process as recited in claim 8 wherein the impure protein fraction comprises Fraction V precipitate.

13. A process as recited in claim 8 wherein both the first and second anion-exchange media used to bind $\alpha_1$-acid glycoprotein a diethylamino ethyl ligand bound to a cross-linked dextran matrix.

14. A process as recited in claim 8 wherein the cation-exchange medium used to bind contaminants is a carboxymethyl ligand bound to a fibrous cellulose matrix.

15. A process for purifying $\alpha_1$-acid glycoprotein comprising:

providing an impure protein fraction comprising $\alpha_1$-acid glycoprotein;

contacting the impure protein fraction with an anion-exchange medium to thereby bind $\alpha_1$-acid glycoprotein present in the impure protein fraction to the anion-exchange medium;

eluting the $\alpha_1$-acid glycoprotein from the anion-exchange medium;

contacting the $\alpha_1$-acid glycoprotein eluted from the anion-exchange medium with a cation-exchange medium;

binding contaminants, but not $\alpha_1$-acid glycoprotein, to the cation-exchange medium; and recovering the $\alpha_1$-acid glycoprotein.

16. A process as recited in claim 15 wherein the $\alpha_1$-acid glycoprotein is eluted from the anion-exchange medium with a sodium chloride solution.

17. A process as recited in claim 16 wherein the concentration of sodium chloride in the sodium chloride solution is 1M.

18. A process as recited in claim 15 wherein the anion-exchange medium used to bind $\alpha_1$-acid glycoprotein is a diethylamino ethyl ligand bound to a cross-linked dextran matrix.

19. A process as recited in claim 15 wherein the cation-exchange medium to bind contaminants is a carboxymethyl ligand bound to a fibrous cellulose matrix.

20. A process as recited in claim 15, wherein the impure protein fraction comprises Fraction V precipitate.

21. A process as recited in claim 15, wherein the impure protein fraction comprises Fraction V supernatant.

22. A process for purifying $\alpha_1$-acid glycoprotein comprising:

providing a Fraction V supernatant comprising $\alpha_1$-acid glycoprotein and contaminants at a pH of from 4.5 to 4.7;

contacting the Fraction V supernatant with an anion-exchange medium comprising a diethylamino ethyl ligand to thereby bind $\alpha_1$-acid glycoprotein to said anion-exchange medium;

eluting the $\alpha_1$-acid glycoprotein from the anion-exchange medium using a 1M NaCl solution to thereby provide an $\alpha_1$-acid glycoprotein eluate;

contacting the $\alpha_1$-acid glycoprotein eluate with a cation-exchange medium to thereby bind remaining contaminants, but not $\alpha_1$-acid glycoprotein, to the cation-exchange medium; and recovering the unbound $\alpha_1$-acid glycoprotein.

23. A process as recited in claim 22 comprising the additional steps of:

after recovering the unbound $\alpha_1$-acid glycoprotein from the cation-exchange medium, contacting the recovered unbound $\alpha_1$-acid glycoprotein with a second anion-exchange medium to thereby bind the $\alpha_1$-acid glycoprotein to said second anion-exchange medium; and eluting the $\alpha_1$-acid glycoprotein from the second anion-exchange medium and recovering the $\alpha_1$-acid glycoprotein.

24. A process for purifying $\alpha_1$-acid glycoprotein consisting essentially of the following steps:

providing an impure protein fraction comprising $\alpha_1$-acid glycoprotein and protein contaminants;

contacting the impure protein fraction with a first anion-exchange medium to thereby bind $\alpha_1$-acid glycoprotein present in the impure protein fraction to the anion-exchange medium;

eluting $\alpha_1$-acid glycoprotein from the anion-exchange medium to provide an $\alpha_1$-acid glycoprotein eluate;

contacting the $\alpha_1$-acid glycoprotein eluate with a cation-exchange medium to thereby bind contaminants but not $\alpha_1$-acid glycoprotein to said cation exchange medium;

recovering the unbound $\alpha_1$-acid glycoprotein from the cation-exchange medium;

binding $\alpha_1$-acid glycoprotein recovered from the cation exchange medium to a second anion-exchange medium; and eluting the $\alpha_1$-acid glycoprotein from the second anion-exchange medium and recovering the $\alpha_1$-acid glycoprotein.

25. A process as recited in claim 24 wherein the $\alpha_1$-acid glycoprotein is eluted from both the first and second anion-exchange media with a solution comprising sodium chloride.

26. A process as recited in claim 25 wherein the concentration of sodium chloride in the sodium chloride solution is 1M.

27. A process as recited in claim 24 wherein the impure protein fraction comprises Fraction V supernatant.

28. A process as recited in claim 24 wherein the impure protein fraction comprises Fraction V precipitate.

29. A process as recited in claim 24 wherein both the first and second anion-exchange media used to bind $\alpha_1$-acid glycoprotein comprise a diethylamino ethyl ligand bound to a cross-linked dextran matrix.

30. A process as recited in claim 24 wherein the cation-exchange medium used to bind contaminants is a carboxymethyl ligand bound to a fibrous cellulose matrix.

31. A process for purifying $\alpha_1$-acid glycoprotein consisting essentially of the following steps:

providing an impure protein fraction comprising $\alpha_1$-acid glycoprotein;

contacting the impure protein fraction with an anion-exchange medium to thereby bind $\alpha_1$-acid glycoprotein present in the impure protein fraction to the anion-exchange medium;

eluting the $\alpha_1$-acid glycoprotein from the anion-exchange medium;

contacting the $\alpha_1$-acid glycoprotein eluted from the anion-exchange medium with a cation-exchange medium;

binding contaminants, but not $\alpha_1$-acid glycoprotein, to the cation-exchange medium; and recovering the $\alpha_1$-acid glycoprotein.

32. A process as recited in claim 31 wherein the $\alpha_1$-acid glycoprotein is eluted from the anion-exchange medium with a sodium chloride solution.

33. A process as recited in claim 32 wherein the concentration of sodium chloride in the sodium chloride solution is 1M.

34. A process as recited in claim 31 wherein the anion-exchange medium used to bind $\alpha_1$-acid glycoprotein is a diethylamino ethyl ligand bound to a cross-linked dextran matrix.

35. A process as recited in claim 31 wherein the cation-exchange medium to bind contaminants is a carboxymethyl ligand bound to a fibrous cellulose matrix.

36. A process for purifying $\alpha_1$-acid glycoprotein consisting essentially of:

providing a Fraction V supernatant comprising $\alpha_1$-acid glycoprotein and contaminants at a pH of from 4.5 to 4.7;

contacting the Fraction V supernatant with an anion-exchange medium to thereby bind $\alpha_1$-acid glycoprotein to the anion-exchange medium comprising a diethylamino ethyl ligand;

eluting the $\alpha_1$-acid glycoprotein from the anion-exchange medium using a 1M NaCl solution to thereby provide an $\alpha_1$-acid glycoprotein eluate;

contacting the $\alpha_1$-acid glycoprotein eluate with a cation-exchange medium to thereby bind remaining contaminants, but not $\alpha_1$-acid glycoprotein, to the cation-exchange medium;

recovering the unbound $\alpha_1$-acid glycoprotein.

\* \* \* \* \*